United States Patent [19]

Horodysky

[11] Patent Number: 4,830,636
[45] Date of Patent: May 16, 1989

[54] HYDROCARBON FUELS CONTAINING SULFONYL DIALKANOL ESTERS

[75] Inventor: Andrew G. Horodysky, Cherry Hill, N.J.

[73] Assignee: Mobil Oil Corporation, New York, N.Y.

[21] Appl. No.: 244,581

[22] Filed: Sep. 13, 1988

Related U.S. Application Data

[60] Division of Ser. No. 36,163, Apr. 7, 1987, abandoned, which is a continuation of Ser. No. 869,445, May 27, 1986, abandoned, which is a continuation of Ser. No. 792,624, Oct. 25, 1985, abandoned, which is a continuation of Ser. No. 612,175, May 21, 1984, abandoned.

[51] Int. Cl.$^4$ .............................................. C10L 1/18
[52] U.S. Cl. ........................................... 44/70; 44/53; 44/56; 44/57; 44/76
[58] Field of Search ................... 44/53, 57, 70, 76, 56

[56] References Cited

U.S. PATENT DOCUMENTS

| | | | |
|---|---|---|---|
| 2,640,848 | 6/1953 | Harman et al. | 252/48.6 |
| 2,812,267 | 11/1957 | Garner et al. | 260/400 |
| 2,846,461 | 8/1958 | Thompson et al. | 44/70 |
| 2,893,952 | 7/1959 | Chenicek | 44/76 |
| 3,501,514 | 3/1970 | Grimm et al. | 260/400 |
| 3,574,101 | 4/1971 | Murphy | 44/70 |
| 3,654,323 | 4/1972 | Clark | 260/400 |
| 4,344,853 | 8/1982 | Gutierrez et al. | 252/48.6 |

FOREIGN PATENT DOCUMENTS 0545631  9/1957  Canada .............................. 260/400

OTHER PUBLICATIONS

CA 84:76603D, Magne et al., vol. 84, 1976.
CA 72:12096k, Bran Nock, vol. 72, 1970.

*Primary Examiner*—William R. Dixon, Jr.
*Assistant Examiner*—Margaret B. Medley
*Attorney, Agent, or Firm*—Alexander J. McKillop; Charles J. Speciale; Van D. Harrison, Jr.

[57] ABSTRACT

New fuel and lubricant compositions are provided which, when used to fuel or lubricate an engine such as an internal combustion engine, help to reduce friction in such engine. It is contemplated that these compositions will also reduce fuel consumption by the engine.

11 Claims, No Drawings

HYDROCARBON FUELS CONTAINING SULFONYL DIALKANOL ESTERS

This is a division of copending application Ser. No. 036,163, filed on Apr. 7, 1987, now abandoned, which is a continuation of application Ser. No. 869,445, filed May 27, 1986, now abandoned, which is a continuation of application Ser. No. 792,624, filed Oct. 25, 1985, now abandoned, which is a continuation of application Ser. No. 612,175, filed May 21, 1984 now abandoned.

BACKGROUND OF THE INVENTION

1. Field of the Invention

The invention relates to lubricant and fuel compositions containing certain additives, and to the additives per se. More particularly, the invention relates to lubricants, greases therefrom and fuels, each having therein a friction reducing amount of a sulfonyl dialkanol ester.

2. Description of the Prior Art

Many means have been employed to reduce overall friction in modern engines, particularly automobile engines. The primary reasons are to reduce the amount of fuel consumed by the engine. While it is commonly understood that lubricants by definition, reduce friction between moving surfaces, friction reducing additives are agents which, when added to lubricants in minor amounts, significantly enhance the frictional properties of those lubricants without significantly modifying other physical properties such as viscosity, density, pour point and the like. It is just as commonly understood that not all additives will reduce friction, that there are no certain criteria to predict such activity, and that even though an additive may be a friction reducer, it may not always reduce fuel consumption.

Many of the solutions to reducing fuel consumption have been strictly mechanical, as for example, setting the engine for a leaner burn, or building smaller cars and smaller engines. However, considerable work has been done with lubricating oils and fuels to enhance their friction properties by modifying them with friction reducing additives.

Although certain esters, for example, have been added to lubricants for various purposes, the reaction products of this invention are, to applicant's best knowledge, novel and they have no prior history of use in lubricant or fuel compositions as friction reducing additives or in the areas of anticorrosion, especially copper corrosion inhibiting antiwear and antioxidation. Further, no art is known which suggests the invention described herein.

SUMMARY OF THE INVENTION

The invention deals with a product which comprises predominantly a compound of the formula

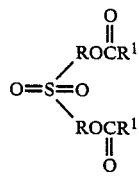

wherein R is a $C_2$ to $C_4$ hydrocarbylene group and $R^1$ is a $C_{10}$ to $C_{30}$ hydrocarbyl group. It deals also with a composition comprising a major proportion of a liquid fuel or a lubricant and a friction reducing amount of the product. It will be understood that the separate R and $R^1$ groups can be the same or different. That is, both R's can be the same or different and both $R^1$'s can be the same or different.

DESCRIPTION OF SPECIFIC EMBODIMENTS

Sulfonyl dialkanol esters (also known as esters of hydroxyalkyl sulfone) demonstrate good friction reducing properties when formulated into fuels or lubricants at low additive concentrations and are expected to improve fuel economy properties of hydrocarbon fuels such as gasoline. These sulfonyl dialkanol diesters can be readily synthesized by the esterification reaction of sulfonyl dialkanols with carboxylic acids or acyl halide as exemplified below:

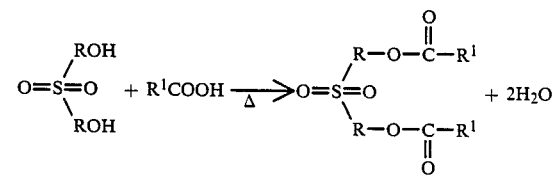

where, as shown above, R can be a $C_2$ to $C_4$ hydrocarbylene group, preferably ethylene, and $R^1$ can be a $C_{10}$ to $C_{30}$ hydrocarbyl group, including decyl, dodecyl, tetradecyl, heptadecyl, octadecyl, eicosyl and triacontyl groups including mixture thereof such as the $C_{12}$ to $C_{15}$ mixed groups. The $C_{12}$ to $C_{18}$ alkyl groups are preferred.

The sulfonyl dialkanol esters can also be formed by the transesterification of a sulfonyl dialkanol with a hydrocarbyl carboxylic acid ester.

The sulfonyl compounds embraced include sulfonyl diethanol, sulfonyl dipropanol and sulfonyl dibutanol. The acids include decanoic acid, dodecanoic acid, tetradecanoic acid, octadecanoic acid, eicosanoic acid and triacontanoic acid, as well as the unsaturated members such as oleic acid and lineoleic acid.

The sulfone dialkanols used herein are readily obtainable from commercial sources or easily made using known methods.

The sulfonyl esters can be made by reacting the sulfone dialkanols with organic acid at from about 100° C. to about 200° C., preferably from about 120° C. to about 170° C. Preferably 2 moles of acid per mole of sulfone dialkanol are used. Times of reaction will vary between about 1 hour or less and about 24 hours. Solvents, such as benzene, toluene and xylene can be used if desired.

One can use the acyl halides to make the products if desired. For example, oleoyl chloride (or another halide) can be used instead of oleic acid to form the sulfonyl ester.

The liquid fuels improved in accordance with the present invention comprise those which are normally susceptible to forming undesirable carburetor and intake valve deposits in internal combustion engines. Specifically, liquid hydrocarbon fuels boiling from about 75° F. to about 750° F., including gasoline, jet fuel and dies fuel may be mentioned. Of particular significance is the treatment of petroleum distillate fuels having an initial boiling point of about 75° F. to about 135° F. and an end boiling point from about 250° F. to about 750° F. It should be noted, in this respect, that the term "distillate fuels" or distillate fuel oils" is not intended to be restricted to straight-run distillate fractions. These distillate fuel oils can comprise straight run distillate fuel oils, catalytically or thermally cracked (including hydrocracked) distillate fuel oils or mixtures of straight run distillate fuel oils, naphthas and the like, with cracked distillate stocks. Moreover, such fuel oils can be treated in accordance with such well known commercial methods as acid or caustic treatment, hydrogenation, solvent refining, clay treatment and the like.

The distillate fuels are characterized by their relatively low viscosity, pour point and the like. The principle property which characterizes these hydrocarbons, however, is their distillate range. As hereinbefore indicated, this range will lie between about 75° F. and about 750° F. Obviously the distillation range of each individual fuel will cover a narrower boiling range, falling nevertheless, within the above-specified limits. Likewise, each fuel will boil substantially continuously throughout its distillation range.

In addition to the hydrocarbon fuels mentioned, other fuels improved by the disclosed additives are alcohols such as methyl alcohol and ethyl alcohol, mixtures thereof and mixtures with the mentioned hydrocarbon fuels.

Particularly contemplated among the fuels or fuel oils are Nos. 1, 2 and 3 fuel oils, used in heating and as diesel fuel oils, gasoline and jet combustion fuels. The domestic fuel oils generally conform to the specifications set forth in ASTM specification D396-48T. Specifications for diesel fuels are defined in ASTM specification D975-48T. Typical jet fuels are defined in military specification MIL-F-624B. In addition, fuel oils of varying viscosity and pour points falling both within and outside the indicated ranges may also be effectively treated through the use of the additives of the present invention.

In general, the disclosed additives are employed in the liquid fuel in a minor amount, i.e., from about 0.001 to about 10 wt % and preferably from about 0.01 to 0.5 wt % based on the total weight of the fuel. The concentration of the additive of this invention in fuels may also be stated in terms of pounds of fuel per 1000 barrels (bbls) thereof. Thus, the additives can be used in the fuel within the range of from about 25 pounds/1,000 barrels to about 500 pounds/1,000 barrels. Any other known additive (as for example, antioxidants and dispersants) generally, may also be used in fuel compositions containing the additives hereof for their known purposes without adverse effect to such compositions.

The disclosed products may also be incorporated in lubricating media which may comprise liquid hydrocarbon oils in the form of either a mineral oil or a synthetic oil, or mixtures thereof, or in the form of a grease, in which any of the aforementioned oils are employed as a vehicle. These can also contain detergents and dispersants, s well as antioxidants, inhibitors, antiwear, extreme pressure, antifoam, pour depressant and viscosity index improving additives without negating the beneficial properties of the novel compositions of this invention. The compositions can include commonly used additives such as calcium or magnesium phenates, sulfonates, polymers, metal or non-metal dithiophosphates, succinimides, and the like. In general, mineral oils employed as the lubricant or grease vehicle may be of any suitable lubricating viscosity range as, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are preferred. The average molecular weights of these oils may range from about 250 to 800. Where the lubricant is to be employed in the form of a grease, the lubricating oil is generally employed in an amoung sufficient to balance the total grease composition, after accounting for the desired quantity of the thickening agent, and other additive components to be included in the grease formulation.

In instances where synthetic oils and mixtures of synthetic oil and mineral oil are desired in preference to mineral oils only, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, di(-butylphthalate) fluorocarbons, silicat eesters, silanes, esters of phosphorus-containing acids, liquid ureas, ferrocene derivatives, hydrogenated mineral oils, chain-type polyphenols, siloxanes and silicones (polysiloxanes), alkyl-substituted diophenyl ethers typified by a butyl-substituted bis(p-penoxyl phenyl) ether, phenoxy phenylethers, etc.

The lubricating vehicles of the aforementioned greases of the present invention, containing the above-described products, are combined with a grease-forming quantity of a thickening agent. For this purpose, a wide variety of materials may be employed. These thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays. In general the product is employed in lubricants in an amount of from about 0.1% to about 10% by weight, and preferably in an amount of from about 0.5% to about 5% by weight of the total weight of the composition.

The following examples are offered to illustrate the invention. It will be understood that their function is to illustrate, not to limit the invention.

EXAMPLE 1

2,2'-Sulfonyl Diethanol and Oleic Acid Reaction Product

Approximately 237 g of a 65% aqueous solution of 2,2'-sulfonyl diethanol, 100 g of benzene and 515 g of oleic acid were placed into a 2 liter reactor equipped with heater, agitator, Dean-Stark tube with condenser and provision for blanketing vapor space with nitrogen. The reactor contents were heated to 110° C. to remove the water present in the starting material and then heated up to 210° C. over a period of 12 hours during which time water of reaction collected furing azeotropic distillation ceased. The product was vacuum topped at 210° C. to remove valatile materials and then filtered through diatomaceous earth. The product was an amber-colored clear fluid.

EXAMPLE 2

2,2-Sulfonyl Diethanol and Oleic Acid Reaction Product

Approximately 345 g of a 65% aqueous solution of 2,2'-sulfonyl diethanol, 100 g of benzene, 150 g of toluene, 846 g of oleic acid and 0.1% of p-toluene sulfonic acid were placed in a reactor as generally described in Example 1. The reactor contents were heated to 99° C. to remove water present in starting materials, and then heated at 155° C. to 175° C. over a period of 22 hours during which time water of reaction collected during azeotropic distillation ceased. The product was vacuum topped at 150° C. and filtered through paper at 50° C. The product was an amber-colored clear fluid which became slightly waxy after cooling.

The products of the examples were evaluated for friction reducing properties by first blending into both synthetic and mineral oil based fully formulated engine oils and then tested using the Low Velocity Friction Apparatus.

LOW VELOCITY FRICTION APPARATUS (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever cam-motor arrangement.

Procedure

The rubbing surfaces and 12-13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone}) - U_k \text{ of Additive plus oil})}{(U_k \text{ of oil alone})} \times 100$$

Thus, the corresponding value for the oil alone would be zero for the form of the date used in the Table below.

TABLE 1

| Friction Test Results Using LVFA | | | |
|---|---|---|---|
| | Additive Conc. In Base Blend, (Wt. %) | % Change in of Friction 5 Ft./Min. | Coefficient in LVFA at 30 Ft./Min. |
| Base Oil A SAE-5W-30 (fully formulated synthetic oil containing a detergent/dispersant/ inhibitor package) | 0 | 0 | 0 |
| Example 1 Plus Base Oil A | 4 | 52 | 36 |
| Example 2 plus Base Oil B | 2 | 52 | 42 |
| Base Oil B-SAE 10W-40 (fully formulated mineral oil containing a detergent/dispersant/ inhibitor package) | 0 | 0 | 0 |
| Example 1 Plus Base Oil B | 2 0.5 | — — | 47 36 |

The coefficients of friction were significantly reduced relative to the base fluids. Reductions in friction of up to 52% were noted with each of the examples tested.

What is claimed is:

1. A fuel composition comprising a major proportion of a liquid hydrocarbon and a friction reducing amount of a product which comprises predominantly a compound of the formula

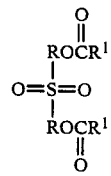

wherein $R^1$ is a $C_{10}$ to $C_{30}$ hydrocarbyl group, and wherein R is a $C_2$ to $C_4$ hydrocarbylene group.

2. The composition of claim 1 wherein $R^1$ is a decyl, dodecyl, tetradecyl, octadecyl, eicosyl, triacontyl, oleyl or lineoleyl group.

3. The composition of claim 1 wherein the compound is a sulfonyl diethanol.

4. The composition of claim 1 wherein the compound is a sulfonyl dipropanol.

5. The composition of claim 1 wherein the compound is a sulfonyl dibutanol.

6. The composition of claim 1 wherein the liquid hydrocarbon is selected from the group consisting of gasoline, alcohol, jet fuel, diesel fuel, and mixtures thereof.

7. The composition of claim 1 wherein the liquid hydrocarbon is gasoline.

8. The composition of claim 1 wherein the liquid hydrocarbon is alcohol.

9. The composition of claim 1 wherein the liquid hydrocarbon is jet fuel.

10. The composition of claim 1 wherein the liquid hydrocarbon is diesel fuel.

11. The composition of claim 1 wherein the concentration of said product is between about 0.001 and about 10 percent by weight of the composition.

* * * * *